(12) United States Patent
Shor et al.

(10) Patent No.: US 7,930,948 B2
(45) Date of Patent: Apr. 26, 2011

(54) DEVICE FOR LEACHING EXTRACTION AND ASSESSMENT

(75) Inventors: Leslie M. Shor, Nashville, TN (US); Andrew Garrabrants, Nashville, TN (US); David S. Kosson, Brentwood, TN (US)

(73) Assignee: Vanderbilt University, Nashville, TN (US)

( * ) Notice: Subject to any disclaimer, the term of this patent is extended or adjusted under 35 U.S.C. 154(b) by 438 days.

(21) Appl. No.: 12/185,799

(22) Filed: Aug. 4, 2008

(65) Prior Publication Data

US 2009/0044605 A1 Feb. 19, 2009

Related U.S. Application Data

(60) Provisional application No. 60/953,894, filed on Aug. 3, 2007.

(51) Int. Cl.
 *G01N 33/00* (2006.01)
 *G01N 1/00* (2006.01)

(52) U.S. Cl. .......................... 73/866; 73/64.56; 73/61.59

(58) Field of Classification Search .................... 73/866, 73/64.56, 61.59
 See application file for complete search history.

(56) References Cited

U.S. PATENT DOCUMENTS

| | | | |
|---|---|---|---|
| 4,759,661 A | | 7/1988 | Nichols |
| 4,783,318 A | * | 11/1988 | Lapakko ........................ 422/101 |
| 7,222,546 B2 | | 5/2007 | St. Germain |
| 7,351,005 B2 | | 4/2008 | Potts |
| 2005/0064524 A1 | * | 3/2005 | Deutsch et al. .............. 435/7.23 |
| 2009/0193880 A1 | * | 8/2009 | Halverson et al. ........... 73/64.56 |

OTHER PUBLICATIONS

Kolpin, D. W., E. T. Furlong, M. T. Meyer, E. M. Thurman, S. D. Zaugg, L. B. Barber and H. T. Buxton (2002). "Pharmaceuticals, Hormones, and Other Organic Wastewater Contaminants in U.S. Streams, 1999-2000: A National Reconnaissance." Environmental Science & Technology, 36, 1202-1211.

Kosson, D. S., H. A. van der Sloot, F. Sanchez and A. C. Garrabrantrs (2002). "An Integrated Framework for Evaluating Leaching in Waste Management and Utilization of Secondary Materials." Environmental Engineering Science, 19(3), 159-204.

Rockne, K. J., L. M. Shor, L. Y. Young, G. L. Taghon and D. S. Kosson (2002). "Distributed Sequestration and Release of Pahs in Weathered Sediment: The Role of Sediment Structure and Organic Carbon Properties." Environmental Science & Technology, 36(12), 2636-2644.

* cited by examiner

*Primary Examiner* — Hezron Williams
*Assistant Examiner* — Nathaniel Kolb
(74) *Attorney, Agent, or Firm* — Stites & Harbison PLLC; Richard S. Myers, Jr.

(57) ABSTRACT

A apparatus and process for quantifying of contaminants, wherein the apparatus comprises a container that includes a housing to support a sample, and a gel elastomer inside the enclosure. The gel elastomer is capable of absorbing the contaminants that are leached from the sample. The gel may be a PDMS gel, and is preferable coated on a, or the side wall of the apparatus. After a period of time, the gel is analyzed for the presence and amount of contaminants.

18 Claims, 3 Drawing Sheets

DEVICE FOR LEACHING EXTRACTION AND ASSESSMENT

PRIOR APPLICATION

This application claims benefit of U.S. Patent Application No. 60/953,894, filed Aug. 3, 2007, the contents of which are incorporated herein by reference.

FIELD OF THE INVENTION

Generally, the present invention relates to the field of quantification of organic contaminants.

SUMMARY OF THE INVENTION

Aspects of the present invention include apparatus, methodology, and applications related to the quantification of mass transfer potential organic contaminants from granular or monolithic samples.

Other aspects include methods for aqueous sample collection (e.g., groundwater or surface water sampling) including where near instantaneous, field extraction of low solubility organic contaminants is desirable to improve accuracy of the analysis.

Features of the apparatus of the present invention include at least customized capacity for small to large sample volumes, granular or monolithic sample forms, material compatibility for simultaneous analysis of metal, hydrophobic organic, and volatile organic contaminant leaching, and high efficiency organic species capture from the aqueous phase and concentration.

Additionally, embodiments of the apparatus of the present invention can be manufactured for a low unit cost and widely adopted by environmental sampling and analysis firms, government agencies, and researchers.

Aspects of the present invention are suitable for laboratory or field applications.

Other aspects of the present invention provide an inexpensive apparatus and method for removing constituent parts of mineral residues through leaching, and determining the extent of leaching expected to occur in natural settings, such as in surface mineral residues (ore supplies, mineral tailings, and the like, for example).

Other aspects of the present invention provide an apparatus which economizes from the standpoint of space, solid sample requirement, and time.

Still, other aspects of the present invention provide an apparatus for determining experimentally the level of contamination to be expected in naturally offering effluents, such as rainwater passing through a bed of mineral including, as stated above, the examples of a stockpile of ore.

Prior art technologies have several drawbacks including high cost, material incompatibility issues making simultaneous analysis of organic and metal constituents impractical, non-quantitative storage, extraction, and recovery of organic constituents (via volatilization, low sorption potential, or irreversible sorption to apparatus), interferences, and low quantification limits.

The unique combination of features make this invention unique among existing apparatus and approaches for measuring leaching potential of contaminants from solid samples.

One embodiment of the present invention is a method of quantifying the leaching potential of an organic sample that comprises providing a container for housing the organic sample. The container comprising a floor, and an inside wall that communicate to form an enclosure, and a gel elastomer located inside the enclosure. The method comprises adding a liquid to the container; housing the sample in the container; allowing a period of time to pass; and measuring a material leached into the gel elastomer. In embodiments, the sample may be supported by a wire stage. An example of the gel elastomer is a PDMS gel.

To increase surface area, the gel elastomer may be coated on the inside wall of the container.

In other embodiments of the present invention, after the allowing a period of time to pass step, the gel elastomer is contacted with a solvent and removed from the container for the following measuring step.

The sample used with embodiments of the present invention can vary. For example, it may be monolithic, granular, compacted granular, solidified waste form, aqueous, a sediment material, derived from soil, or soil. The aqueous sample is a groundwater sample.

Other embodiments of the present invention include an apparatus that has a floor, and a wall, with the floor, and wall, communicating to make an enclosure; a housing inside the enclosure to support a sample; and a gel elastomer inside the enclosure. The gel elastomer should be capable of absorbing and retaining components that are leached from the sample. In embodiments of the present invention, the gel elastomer is an organo-silicon gel elastomer. In further embodiments of the present invention, the gel is a PDMS gel.

In embodiments of the present invention, the gel elastomer can be coated on the wall of the container.

In embodiments of the present invention, the floor and wall are glass to form a glass container. In other embodiments, the enclosure is about a one-liter glass container. A lid capable of communicating with the wall to enclose and seal the enclosure can be used.

In embodiments of the present invention, the housing to support the sample is a wire stage on which a sample can rest.

Another embodiment of the present invention is the sample and container in combination. This can include embodiments where the combination comprises a contaminated sample; and an apparatus as described herein.

DESCRIPTION OF THE INVENTION

Figure 1:
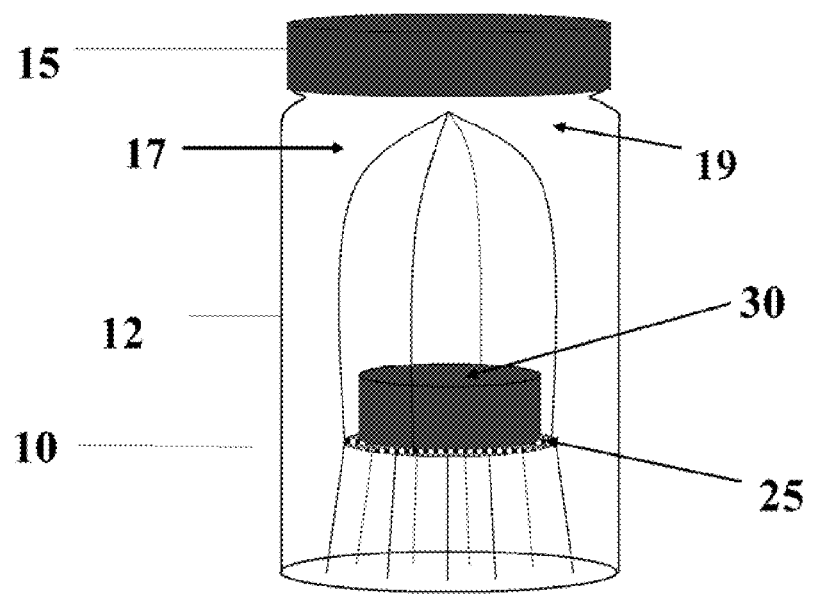
FIG. 1 is a diagram showing an embodiment of the present invention. More specifically, it is a schematic of a reaction vessel of the present invention showing a wire holder and a monolithic sample.

As indicated above, and aspect of the present invention is an enclosed apparatus that has a housing inside the enclosure to support a sample and a gel elastomer inside the enclosure. An example of such an apparatus 10 is presented in FIG. 1. This embodiment is represented by a glass jar. This embodiment 12 also includes a lid 15. Further, the gel elastomer 12 is coated in the wall of the container. Inside the container is a liquid medium 17. A sample 30 to be analyzed rests on a stage 25 below the liquid line 19.

Aspects of the present invention allow direct quantification of leachable organic constituents from within solid materials.

Such measurements are central to evaluating the environmental compatibility of solid materials (e.g., sediments, soils, solidified waste forms) containing organic constituents that have the potential to degrade water resources or be taken up by biota and the food chain. These measurements also facilitate the evaluation of bioavailability of organic constituents. The present invention is designed to simplify current difficulties in assessing leaching of organic constituents with low aqueous solubility, such as, but not limited to, polyaromatic hydrocarbons (PAHs) and polychlorinated biphynels (PCBs).

Methods of the present invention include measuring leaching rate and extent for organic constituents from monolithic, compacted granular and granular materials.

The apparatus of the present invention can be used to for aqueous sample collection (e.g., groundwater or surface water sampling) where near-instantaneous, field extraction of low solubility organic contaminants is desirable to improve accuracy of the analysis.

In an embodiment of the present invention, one may coat the interior side surface of a glass jar with a gel elastomer with a capacity to reversibly absorb organic compounds from water. In one example, the gel elastomer may be polydimethyl siloxane (PDMS), or an organo-silicon gel elastomer. The amounts used can include a relatively large quantity (e.g., ca. 40 g).

Similar materials are currently used in a method called "solid phase micro-extraction" to quantify the aqueous concentration of a wide range of organic compounds from aqueous samples. In that application, when the distribution between aqueous and gel concentrations is known a priori, the aqueous concentration in an unknown sample can be computed from equilibration with and subsequent extraction of sorbed constituents contained within a silicon filament.

In embodiments of the present invention, a material is used to absorb aqueous organic compounds from water, but, by virtue of using a greater quantity of the gel sorbent, near-depletion of organics in the water phase can be maintained.

This design feature allows determination of the inherent mass transfer resistance of a material, and to predict the leaching potential under many different environmental exposure scenarios. Also, the inherent integrated nature of the design provides a constituent trapping function, substantially decreases the potential for semi-volatile compounds like naphthalene to be lost from the system due to volatilization. Following a testing interval, sorbed compounds can be re-eluted by emptying the contents of the vessel and adding, for example, a small volume (such as ca. 1/100 of the original aqueous volume) of an organic solvent such as acetonitrile.

The coating is also an elegant means to concentrate compounds of interest within the leaching test container, without the need for any additional transfers or complex physical or chemical separations. Solid particles including colloids are not absorbed into the gel matrix and do not stick to the PDMS surface, so compounds must pass into the aqueous phase before they are absorbed, providing an accurate measure of diffusion potential from a solid into water, the universal environmental solvent. This feature is not shared by the main alternatives to this system, as described below.

Standard methods apparatus currently do not allow measurement of leaching potential of organic compounds under conditions compatible with modeling of realistic environmental exposure scenarios.

In other embodiments of the present invention, a non-aqueous phase liquid is added to the system, such as hexane, but this approach has a potential drawback of also extracting organic compounds bound to suspended solids or colloids as well as truly dissolved constituents. Another alternative is to use a suspended solid phase, such as micro-porous hydrophobic beads like Tenax, but these materials are very costly (ca. $100/10 g, versus $30 for 500 g PDMS) and use of dispersed Tenax can pose operational difficulties. The beads are very small and disperse over the surface of the water; separating them from the experimental apparatus and physically collecting them together for extraction of sorbed constituents is difficult. The beads can also retain colloids in small pores, and are difficult to re-extract quantitatively after long contact times with hydrophobic organic contaminants. In applications where the beads can be packed together in a cartridge and the leachate is circulated through the cartridge (known as a "Tenax trap"), circumvents the problem of gathering the Tenax beads together. However, not all applications involve mixing or recirculating leaching fluid. Thus, the use of Tenax may require additional operational complexity and cost. In addition, complete removal of colloids from solution using filtration is nearly impossible, so recirculating tests with Tenax trap cartridges may over-estimate leaching potential by including particle- or colloid-sorbed particles entrained in the Tenax bed as the "aqueous" fraction. Since the equilibrium partitioning of hydrophobic organic compounds favor particle-associated states over aqueous phases by many orders of magnitude, this can be a very big problem operationally. Also, column studies require some metal or plastic parts, or both, causing incompatibilities with organic or metal analysis.

EXAMPLES

The following examples are offered for exemplary purposes only. It is intended to demonstrate at least one embodiment of the present invention and is not to be construed as being limiting thereof.

Preparing an apparatus of the present invention: The procedure for preparing coated jars is as follows: Sylgard 184 silicon elastomer is mixed with curing agent vigorously for 2 minutes and degassed in a vacuum to remove trapped gases. Then, an aliquot of uncured elastomer (about 40 g) is poured onto the inside wall of a clean glass jar (we have used 1 L jars in our testing, but the concept could be applied to jars of any size). These jars are then rolled flat on their side at a slow rate of revolution (ca. 6 rpm) for 12 hours at 30° C. for a soft-cure to prepare a uniform optically-transparent coating on the inside walls. Then the jars are baked at 60° C. for 12 hours to set the PDMS in place.

Coated jars are used in leaching tests by suspending a solid sample (which could be a monolithic solid, granular material, etc.) immersed in water on a wire filament support near the center of the vessel (FIG. 1). At discreet time intervals, the sample on the metal carrier is moved to a waiting coated vessel, and the sorbed constituents are extracted from the first vessel with 10 ml acetonitrile by rolling at a high revolution (ca. 30 rpm) for 12 hours. The present inventors have found quantitative extraction of a broad range of hydrophobic organics compounds using the method.

Demonstration Data for the Present Invention Device in PAH Leachate Testing:

This example demonstrates a method of the present invention via the Vanderbilt Mass-Transfer in Monolithic Material (MT3) testing protocol of polycyclic aromatic hydrocarbon (PAH) leaching from a model solidified solid. The MT3 testing protocol is derived from tank leaching procedures for inorganic materials (Kosson et al. 2002) with modifications made to address the low aqueous solubility and potential vaporization of organic compounds, including (but not limited to) polycyclic aromatic hydrocarbons (PAHs). The data from this test can be used to model leaching of constituents from low-permeability materials under realistic field exposure scenarios.

The present invention provides a highly effective means to sequester compounds of interest within the leaching test container, substantially in excess of the limited aqueous solubility of hydrophobic organic compounds, and minimizing volatile losses. In addition, a one-liter capacity apparatus is quantitatively extractable with about 8 ml of acetonitrile, providing a significant concentration effect allowing detection of compounds not otherwise detectible in water even at saturation concentrations. In short, the capabilities demonstrated here are high-resolution, highly reproducible leachate testing of monolithic samples, with ultra low-level detection limits, minimal volatile losses, and material compatibility with other testing needs (i.e., simultaneous testing of metals in the leachate).

The performance data given here demonstrate one application of the technology, but many other applications are encompassed in the scope of this application, including other solids, other constituents of interest, other test methods, environmental sample storage, and field assessments of organic chemical content and mobility. The test data given here tends to demonstrate a strong likelihood for excellent performance in these other applications as well.

Characteristic Properties of PAHs

PAHs are a class of aromatic hydrocarbon compounds that are commonly detected in the environment (Kolpin et al. 2002) via releases from both natural and anthropogenic processes. PAHs are present in naturally-occurring petroleum deposits, in oil spills, and are formed by the incomplete combustion of organic matter, including by forest fires or automobiles. The hydrophobicity of PAHs, often characterized by the octanol/water partition coefficient or $K_{ow}$, increases with molecular weight. Hydrophobic PAHs tend to accumulate in soil and sediment, and tend to be found only in low concentrations freely dissolved in water, or in air (Mackay et al. 1992). The maximum aqueous solubility of many PAHs is below analytical detection limits using state-of-the art techniques including gas chromatography/mass spectroscopy (GC/MS) or high-performance liquid chromatography (HPLC). Some PAHs, especially benzo(a)pyrene, are suspected human carcinogens. PAHs are included in the EPAs priority list of persistent and bioaccumulative toxins. The properties of the sixteen EPA Priority PAHs are given below.

TABLE 1

Properties of the 16 EPA Priority PAHs (after (Mackay et al. 1992).

| Name | Number of Rings | Molecular Mass [g/mol] | Aqueous Solubility [mg/L] | $\log(K_{ow})$ |
|---|---|---|---|---|
| Naphthalene | 2 | 128 | 34.4 | 3.37 |
| Acenaphthylene | 3 | 152 | 3.93 | 4.07 |
| Acenaphthene | 3 | 152 | 3.88 | 4.03 |
| Fluorene | 3 | 166 | 1.9 | 4.18 |
| Phenanthrene | 3 | 178 | 1.29 | 4.57 |
| Anthracene | 3 | 178 | 0.073 | 4.54 |
| Benzo(a)anthracene | 3 | 228 | 0.014 | 5.91 |
| Dibenzo(a,h)anthracene | 3 | 278 | 0.0005 | 7.19 |
| Fluoranthene | 4 | 202 | 0.26 | 5.22 |
| Pyrene | 4 | 202 | 0.35 | 5.18 |
| Benzo(a)pyren | 4 | 252 | 0.0038 | 6.50 |
| Chrysene | 4 | 228 | 0.002 | 5.91 |
| Benzo(b)fluoranthene | 4 | 252 | 0.0015 | 6.50 |
| Benzo(k)fluoranthene | 4 | 252 | 0.00081 | 6.84 |
| Indeno(1,2,3-cd)pyrene | 4 | 276 | 0.00019 | 7.66 |
| Benzo(g,h,i)perylene | 5 | 276 | 0.00026 | 6.85 |

Monolithic Leaching Test Procedure

In the MT3 procedure using the present invention, a sample of monolithic solid test material, including monolithic materials like cement-stabilized contaminated soils, is suspended on a wire holder in a 1-L glass Class 3 environmental storage jar (I-Chem Brand, Chase Scientific Glass, Inc, Rockwood, Tenn.) containing deionized (DI) water at a liquid-to-surface area (L/Sa) ratio of approximately 10 mL/cm$^3$ (FIG. 1). The concentration of PAHs in the leaching solution is maintained below equilibrium by coating the jar with 40 g of polydimethylsiloxane (PDMS) (Sylgard 184 Silicone Elastomer, Dow Corning Co., Corning N.Y.) an organic polymer, used as a high-capacity absorptive sink for organic species. At specified intervals, the sample and carrier are removed from the reaction vessel and placed into a waiting vessel containing fresh leachant and PDMS sorbent. Samples are transferred and the leachate and PDMS phase are characterized at the following cumulative leaching times: 3, 6, 12 hours, 1, 2, 4, 8, 16 days, 1, 2, 3, 4, 5, 6 months. This progression may be continued at 1 month intervals until the desired number of data points have been collected, i.e., when depletion of PAHs from the monolithic solid is achieved.

Aliquots of leachate from each reaction vessel can be characterized for multiple characteristics, including (i) pH and conductivity, (ii) aqueous organic contaminant concentration, including PAH concentration, and (iii) concentration of anions, dissolved organic carbon (DOC), and major and minor metal elements. Organic constituents including PAHs absorbed in the PDMS coating are extracted at 35° C. using approximately 8 mL of acetonitrile and analyzed via HPLC. The leached amounts of PAHs are compared with the total chemical content of the parent material to determine constituent release as a function of leaching time under the experimental conditions.

Lab-Formulated ISS Material (Control Material)

In order to facilitate development and validation of new leaching techniques for PAH-contaminated materials, a control material with well-characterized and homogeneous physical and chemical properties was created from soil, coal tar and cement. This material is referred to as CSS, and its formulation is intended to be similar to in-situ solidified (ISS) materials, which are contaminated soils or other solids that have been field-treated with solidification agents especially cement to reduce the environmental mobility of contaminants of interest. There are currently no adequate testing protocols to measure leaching potential of organic compounds like PAHs from monolithic materials like ISS soils.

Soil: A well-characterized silt loam, collected from Quakertown, N.J. and retained from previous studies, was used as the soil component in the control material. Physical and chemical properties of Quakertown Soil are shown in Table 2. The soil was air dried (~3% moisture content) and passed through a 2-mm stainless steel sieve prior to treatment.

TABLE 2

Physical and Chemical Characteristics of Quakertown Soil used to Formulate the Control Material (after Unger, 1996)

| Characteristic | Quakertown Soil |
|---|---|
| Sand [wt %] | 20 |
| Silt [wt %] | 60 |
| Clay [wt %] | 20 |
| Texture | Silt Loam |
| Organic Matter [wt %] | 3.9 |
| pH | 6.8 |
| Specific Surface Area [m$^2$/g] | 9.75 |

Coal Tar: Approximately 4-L of coal tar was collected in 1-L jars from an electric power utility and sent to Vanderbilt University. The four 1-L jars were homogenized and PAH contents analyzed according to methods described in elsewhere (Rockne et al. 2002). Table 3 shows the mean PAH signature of the coal tar.

TABLE 3

Composition of Coal Tar used in Control Material

| PAH | Concentration [g/kg] |
|---|---|
| Naphthalene | 71.1 |
| Acenaphthylene | 27.7 |
| Acenaphthene | 22.8 |
| Fluorene | 18.5 |
| Phenanthrene | 22.9 |
| Anthracene | 6 |
| Fluoranthene | 12.6 |
| Pyrene | 12.2 |
| Benzo(a)anthracene | 3.0 |
| Chrysene | 3.5 |
| Benzo(b)fluoranthene | 1.9 |
| Benzo(k)fluoranthene | 1.2 |
| Benzo(a)pyrene | 3.9 |
| Dibenzo(a,h)anthracene | 0.3 |
| Benzo(g,h,i)perylene | 1.5 |
| Indeno(1,2,3-cd)pyrene | 1.6 |
| Total 16 EPA PAHs | 210.7 |

Portland Cement: Type I Portland cement (LaFarge, Pasco, Wash.) was used as the binder media for the control material. The cement was passed through a 1-mm stainless steel sieve prior to use in order to remove potential aggregates.

Formulation and Curing: The object of the control material treatment recipe was to obtain a hardened solidified product which was representative of ISS treatment recipes and contained PAH concentrations compatible with analytical capabilities. The final recipe is shown in Table 4.

TABLE 4

Treatment recipe for Lab-Formulated Control Material

| Component | Control Material [wt %] |
|---|---|
| Coal Tar | 4.2 |
| Quakertown Soil | 68.2 |
| Portland Cement | 10.5 |
| Deionized Water | 17.1 |

Treatment components were combined in a 30-L stainless steel mixing bowl using a Univex SRM-30 planetary mixer (Univex Corp., Salem, N.H.). The sequence of steps for mixing the treatment recipe (i) mixing the soil and coal tar together creating a "contaminated soil", blending in the Portland cement, and (iii) adding in deionized (DI) water. Components were mixed until homogenized (approximately 2 mins) for each step.

Figure 2:
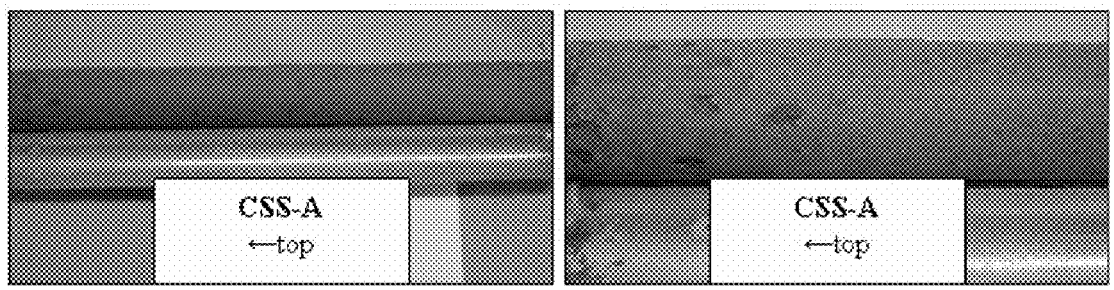
FIG. 2 is a photograph that shows control material (CSS) Core after more than 28 days of curing.

Steps for Creating Lab-Formulated ISS Material (CSS): The treated material was packed into 6.4-cm diameter by 75-cm long stainless steel split core tubes in order to simulate the geometry of the field-core materials. The side seams of the split core tubing were sealed with aluminum tape and duct tape. Compaction consisted of tapping the core tube on the ground 5-10 times for each ⅕ of the tube. When full, the cores were sealed and allowed to cure for 7 days at room temperature before being refrigerated at 4° C. for a minimum of 21-days (total cure time >28 days) prior to use. The resultant control material cores were much more homogenous than the field cores (FIG. 2) and, thus, more appropriate for validation of developed protocols.

Figure 3:
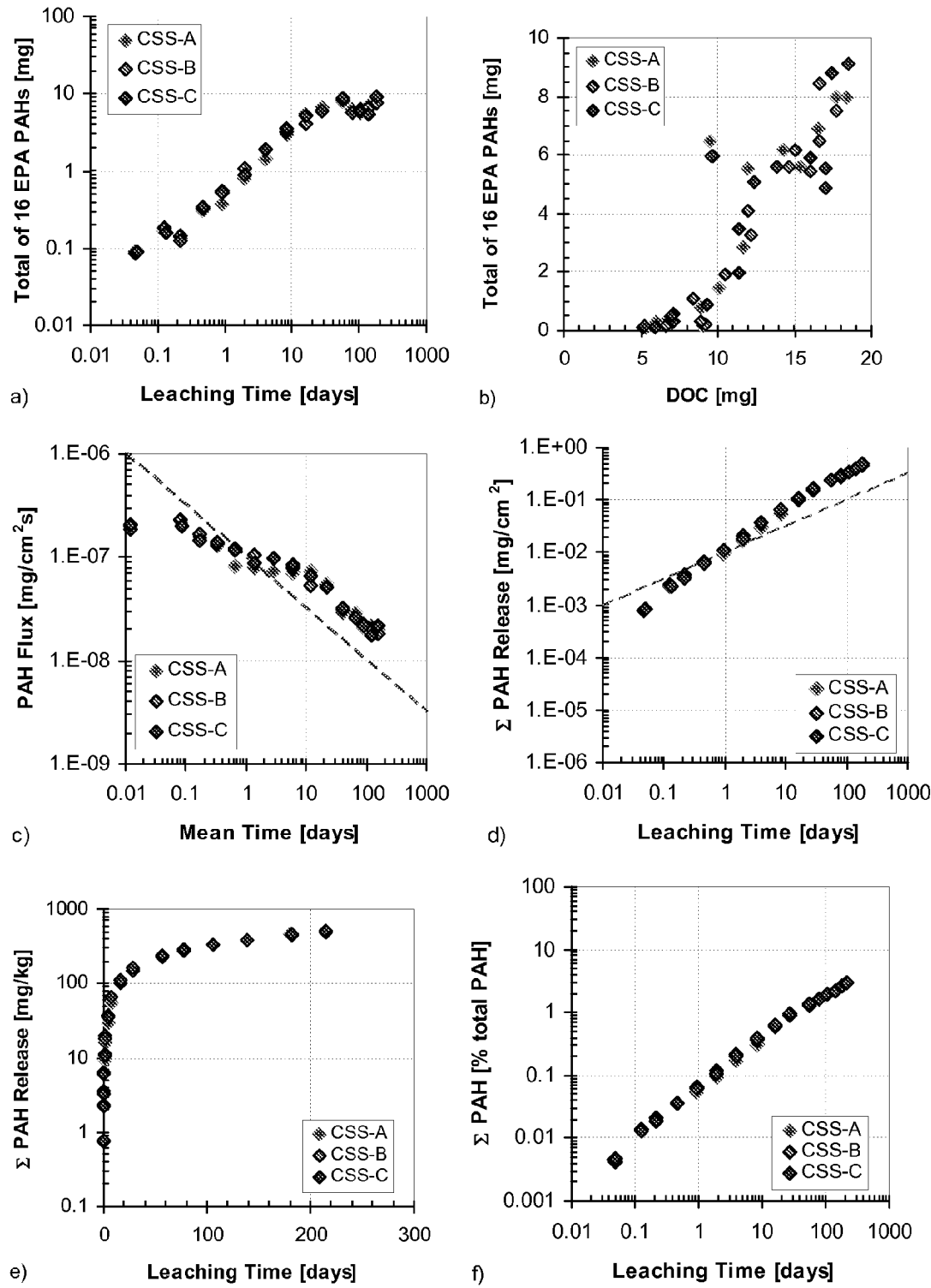
FIG. 3 shows performance data of embodiments of the present invention in testing leaching of PAHs from the control material CSS.

Validation Data: The use of the present invention in the MT3 test for triplicate CSS test materials is shown in FIG. 3. The data show extraordinary performance: replicate tests are very tightly grouped, and performance does not diminish even after more than 6 months continuous testing. Several technical implications of the test results are given below The slopes of the Total 16 EPA PAH release curves for flux and cumulative release are roughly parallel with reference line indicating that PAH release is potentially dominated by diffusion (panels c, d).

PAH mass release appears to be at least somewhat correlated to dissolved organic carbon (DOC) mass (panel b) in all field materials.

PAH cumulative release does not show signs of approaching a limiting value for any of the test materials (panel e). Additional leaching time is required to allow cumulative PAH release to come to a limiting value.

After ~200 days of leaching, cumulative release of Total 16 EPA PAHs is about 3%.

Figure 4:
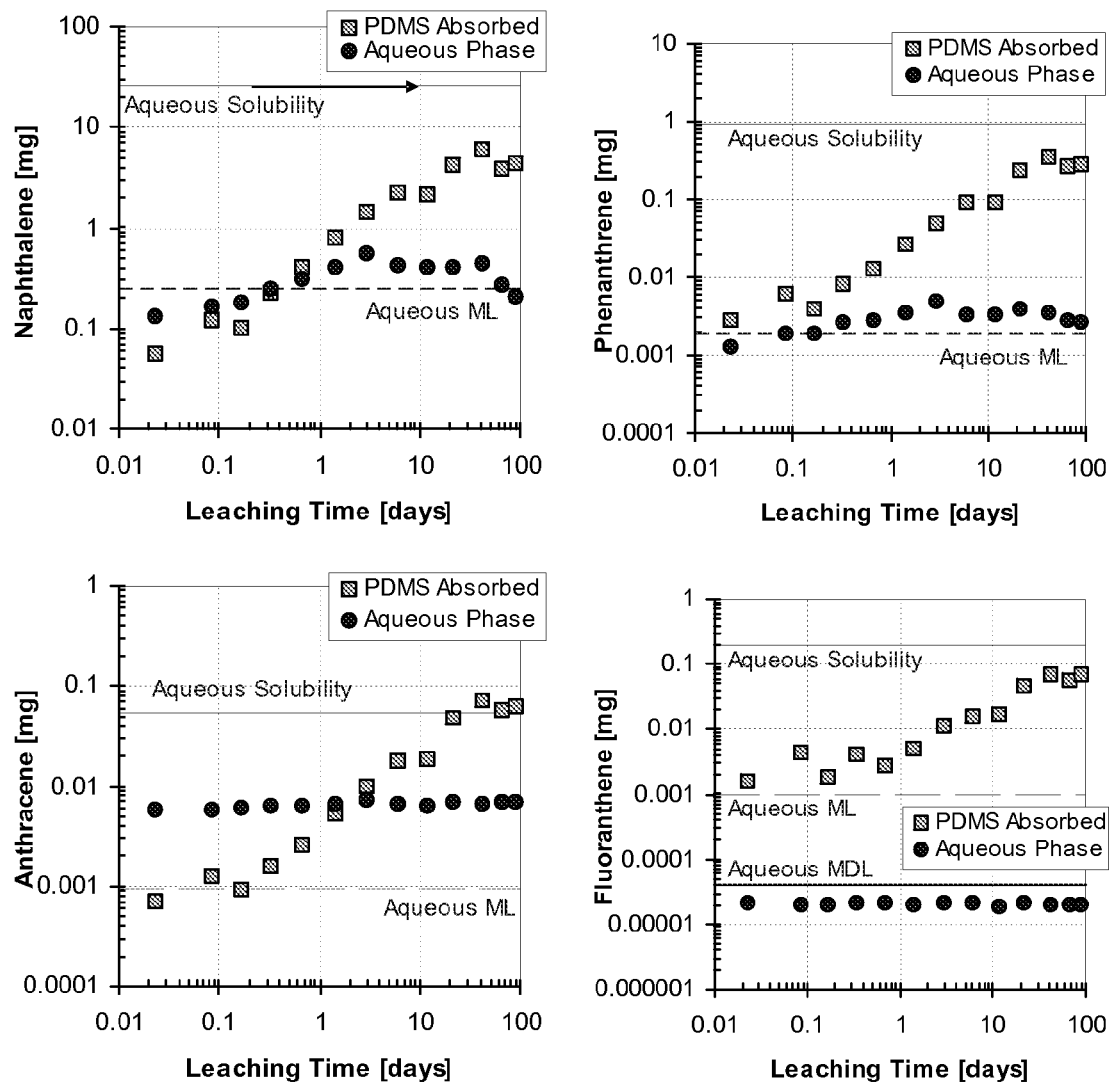
FIG. 4 shows a comparison of aqueous and absorbed masses of individual PAHs in MT3 test of CSS.

FIG. 4 shows further validation of performance of the present invention by comparing PAH mass measured in aqueous leachates and extracted from the coating of individual leaching intervals of MT3 leachates. The coating in the apparatus provides a sink for PAHs which would normally approach equilibrium in the liquid phase and limit mass transfer from the solid. The mass of PAH in the aqueous phase remains significantly below the mass associated with the theoretical aqueous solubility limit (FIG. 4). Without the present invention, material, aqueous solubility would rapidly be approached or exceeded, invalidating the test protocol by inhibiting the true release potential of organic constituents, and requiring vastly increased and unrealistically large device capacity, or excessively frequent sample-vessel exchanges.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the Specification and Example be considered as exemplary only, and not intended to limit the scope and spirit of the invention.

Unless otherwise indicated, all numbers expressing quantities of ingredients, properties such as reaction conditions, and so forth used in the Specification and Claims are to be understood as being modified in all instances by the term "about."Accordingly, unless indicated to the contrary, the numerical parameters set forth in the herein are approximations that may vary depending upon the desired properties sought to be determined by the present invention.

Notwithstanding that the numerical ranges and parameters setting forth the broad scope of the invention are approximations, the numerical values set forth in the experimental or example sections are reported as precisely as possible. Any numerical value, however, inherently contain certain errors necessarily resulting from the standard deviation found in their respective testing measurements.

Throughout this application, various publications are referenced. All such references, specifically including those listed below, are incorporated herein by reference.

REFERENCES

Kolpin, D. W., E. T. Furlong, M. T. Meyer, E. M. Thurman, S. D. Zaugg, L. B. Barber and H. T. Buxton (2002). "Pharmaceuticals, Hormones, and Other Organic Wastewater Contaminants in U.S. Streams, 1999-2000: A National Reconnaissance." *Environmental Science & Technology*, 36, 1202-1211.

Kosson, D. S., H. A. van der Sloot, F. Sanchez and A. C. Garrabrantrs (2002). "An Integrated Framework for Evaluating Leaching in Waste Management and Utilization of Secondary Materials." *Environmental Engineering Science*, 19(3), 159-204.

Mackay, D., W. Y. Shiu and K. C. Ma (1992). *Illustrated Handbook of Physical-Chemical Properties and Environmental Fate for Organic Chemicals: Polynuclear Aromatic Hydrocarbons, Polychlorinated Dioxins, and Dibenzofurans*, Chelsea, Mich., Lewis Publishers.

Rockne, K. J., L. M. Shor, L. Y. Young, G. L. Taghon and D. S. Kosson (2002). "Distributed Sequestration and Release of Pahs in Weathered Sediment: The Role of Sediment Structure and Organic Carbon Properties." *Environmental Science & Technology*, 36(12), 2636-2644.

We claim:

1. A method of quantifying the leaching potential of an organic sample, comprising:
    providing a container for housing the organic sample, said container comprising a floor, and an inside wall that communicate to form an enclosure, and a gel elastomer located inside the enclosure;
    adding a liquid to the container;
    housing the sample in the container;
    allowing a period of time to pass; and
    measuring a material leached into the gel elastomer.

2. The method of claim 1, wherein the sample is supported inside the container by a wire stage.

3. The method of claim 1, wherein the gel elastomer is coated on the inside wall of the container.

4. The method of claim 3, wherein the gel elastomer is PDMS gel.

5. The method of claim 1, wherein after the allowing a period of time to pass step, the gel elastomer is contacted with a solvent and removed from the container for the following measuring step.

6. The method of claim 1, wherein the sample is monolithic, granular, compacted granular, solidified waste form, aqueous, a sediment material, or soil.

7. The method of claim 6, wherein the aqueous sample is a groundwater sample.

8. The method of claim 1, wherein the gel is a PDMS gel.

9. An apparatus, comprising:
    a floor, and a wall, wherein the floor, and wall, communicate to make an enclosure;
    a housing inside the enclosure to support a sample;
    a gel elastomer inside the enclosure, wherein the gel elastomer absorbs and retains components that are leached from the sample, and wherein the gel elastomer is coated on the wall of the container.

10. The apparatus of claim 9, wherein the gel elastomer is an organo-silicon gel elastomer.

11. The apparatus of claim 10, wherein the gel is a PDMS gel.

12. The apparatus of claim 9, wherein the floor and wall are glass to form a glass container.

13. The apparatus of claim 9, wherein the enclosure is about a one-liter glass container.

14. The apparatus of claim 9, wherein the housing to support the sample is a wire stage on which a sample can rest.

15. The apparatus of claim 9, further comprising a lid capable of communicating with the wall to enclose and seal the enclosure.

16. In combination,
    a contaminated sample; and
    an apparatus that comprises a floor, and a wall, wherein the floor, and wall, communicate to make an enclosure;
    a housing inside the enclosure to support the contaminated sample;
    a PDMS gel elastomer coating the wall of the container that is capable of absorbing and retaining components that are leached from the sample.

17. The combination of claim 16, wherein the contaminated sample is a monolithic sample.

18. The combination of claim 16, wherein the contaminated sample is derived from a soil sample.

* * * * *